US012788954B2

(12) United States Patent
Koch

(10) Patent No.: US 12,788,954 B2
(45) Date of Patent: Nov. 10, 2026

(54) MUCOSA PERFORATION

(71) Applicant: LTS LOHMANN THERAPIE-SYSTEME AG, Andernach (DE)

(72) Inventor: Andreas Koch, Melsbach (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 818 days.

(21) Appl. No.: 18/023,771

(22) PCT Filed: Aug. 25, 2021

(86) PCT No.: PCT/DE2021/100715
§ 371 (c)(1),
(2) Date: Feb. 28, 2023

(87) PCT Pub. No.: WO2022/042799
PCT Pub. Date: Mar. 3, 2022

(65) Prior Publication Data

US 2024/0024647 A1 Jan. 25, 2024

(30) Foreign Application Priority Data

Aug. 28, 2020 (DE) ..................... 10 2020 122 557.1

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61K 9/006* (2013.01);
(Continued)

(58) Field of Classification Search
CPC ...... A61M 37/0015; A61M 2037/0023; A61M 2037/0061; A61K 9/0021; A61K 9/006
(Continued)

(56) References Cited

U.S. PATENT DOCUMENTS

2007/0161964 A1* 7/2007 Yuzhakov ......... A61M 37/0015 604/272
2009/0099502 A1 4/2009 Tokumoto et al.
(Continued)

FOREIGN PATENT DOCUMENTS

CA 3125807 A1 7/2020
CN 1658840 A 8/2005
(Continued)

OTHER PUBLICATIONS

PCT IPRP (PCT/DE2021/100715) Nov. 4, 2022 (7 pages).
(Continued)

*Primary Examiner* — Phillip A Gray
(74) *Attorney, Agent, or Firm* — Lippes Mathias LLP

(57) ABSTRACT

The present invention relates to a kit comprising at least one microneedle system and at least one dosage form for transmucosally administering at least one pharmaceutically active ingredient, wherein the at least one dosage form for transmucosal administration comprises at least one pharmaceutically active ingredient, preferably an oral thin film, to this kit for use in the treatment of a patient, to the use of a microneedle system for reducing the permeation barrier of a mucosa for at least one pharmaceutically active ingredient, and to a method for treating a patient, wherein a microneedle system is firstly applied to a point of a mucosa of a patient and is removed again, and then an oral thin film comprising at least one matrix polymer and at least one pharmaceutically active ingredient is applied to the point of the mucosa where the microneedle system was applied and removed
(Continued)

again, or wherein the microneedle system is applied to the mucosa simultaneously with a dosage form for transmucosally administering at least one pharmaceutically active ingredient. The present invention also relates to a biodegradable microneedle system comprising at least one pharmaceutically active ingredient and at least one biodegradable polymer.

13 Claims, 10 Drawing Sheets

(52) U.S. Cl.
CPC ............... *A61M 2037/0023* (2013.01); *A61M 2037/0061* (2013.01)

(58) Field of Classification Search
USPC ............................................................ 604/22
See application file for complete search history.

(56) References Cited

U.S. PATENT DOCUMENTS

| | | | |
|---|---|---|---|
| 2010/0047327 A1* | 2/2010 | Kuwahara .............. | A61K 39/39 514/513 |
| 2010/0312191 A1 | 12/2010 | Allen et al. | |
| 2011/0150946 A1 | 6/2011 | Al-Ghananeem | |
| 2016/0128947 A1 | 5/2016 | McConville et al. | |
| 2017/0080613 A1 | 3/2017 | Asai et al. | |
| 2018/0271777 A1 | 9/2018 | Golubovic-Liakopoulos et al. | |
| 2019/0022022 A1 | 1/2019 | Schobel et al. | |

FOREIGN PATENT DOCUMENTS

| | | | |
|---|---|---|---|
| CN | 102039000 | A | 5/2011 |
| CN | 108837299 | A | 11/2018 |
| CN | 209316551 | U | 8/2019 |
| EP | 2296557 | A1 | 3/2011 |
| WO | 2003070227 | A1 | 8/2003 |
| WO | 03105800 | A2 | 12/2003 |
| WO | 2008093772 | A1 | 8/2008 |
| WO | 2009142741 | A1 | 11/2009 |
| WO | 2010140760 | A2 | 12/2010 |
| WO | 2014164314 | A1 | 10/2014 |
| WO | 2014188276 | A2 | 11/2014 |
| WO | 2016155082 | A1 | 6/2016 |
| WO | 2017186563 | A1 | 11/2017 |
| WO | 2017192923 | A1 | 11/2017 |
| WO | 2018091473 | A1 | 5/2018 |
| WO | 2019067667 | A1 | 4/2019 |
| WO | 2020144345 | A1 | 7/2020 |

OTHER PUBLICATIONS

PCT IPRP Translation (PCT/DE2021/100715) Nov. 4, 2022 (6 pages).

Guillot, "Microneedle-Based Delivery: An Overview of Current Applications and Trends", Pharmaceutics 2020, 12, 569; doi:10.3390/pharmaceutics12060569 www.mdpi.com/journal/pharmaceutics (27 pages) Jun. 19, 2020.

PCT ISR Translation, (PCT/DE2021/100715) Dec. 22, 2021 (3 pages).

1st Exam Report, (DE 10 2020 122 557.1) Dec. 2, 2021 (5 pages).

* cited by examiner

MUCOSA PERFORATION

This application is a National Stage Entry of International Application No. PCT/DE2021/100715, filed Aug. 25, 2021, and claims the priority benefit of German Patent Application No. 10 2020 122 557.1, filed Aug. 28, 2020, the contents of which are incorporated by reference herein.

The present invention relates to a kit comprising at least one microneedle system and at least one dosage form for transmucosally administering at least one pharmaceutically active ingredient, wherein the at least one dosage form for transmucosal administration comprises at least one pharmaceutically active ingredient, preferably an oral thin film, to this kit for use in the treatment of a patient, to the use of a microneedle system for reducing the permeation barrier of a mucosa for at least one pharmaceutically active ingredient, and to a method for treating a patient, wherein a microneedle system is firstly applied to a point of a mucosa of a patient and is removed again, and then an oral thin film comprising at least one matrix polymer and at least one pharmaceutically active ingredient is applied to the point of the mucosa where the microneedle system was applied and removed again, or wherein the microneedle system is applied to the mucosa simultaneously with a dosage form for transmucosally administering at least one pharmaceutically active ingredient. The present invention also relates to a biodegradable microneedle system comprising at least one pharmaceutically active ingredient and at least one biodegradable polymer.

Pharmaceutically active ingredients can be administered via the mucosa with appropriate dosage forms. For example, oral thin films are suitable for this purpose.

Oral thin films (OTFs) are thin films containing at least one pharmaceutically active ingredient that are placed directly against a mucosa (mucous membrane), preferably the oral mucosa, and preferably dissolve there. These films are, especially, thin active-ingredient-containing polymer-based films which, when applied to a mucous membrane, especially the oral mucosa, deliver the active ingredient directly into same.

This dosage form has the advantage that the active ingredient is absorbed for the most part by the oral mucosa for example, thus avoiding the first-pass effect, which occurs in the case of the conventional dosage form of an active ingredient in tablet form. The active ingredient in this case may be dissolved, emulsified or dispersed in the film.

On account of the good vascular supply and the strong blood flow of the oral mucosa in this area, the active ingredient is absorbed quickly there especially.

The absorption path via the oral mucosa is thus distinguished by a relatively quick active ingredient passage or also active ingredient permeation.

For example, following application of a nicotine-containing OTF, an effective increase in blood pressure can be measured as pharmacological evidence already after two minutes.

OTFs are therefore also preferably used for indications that require a rapid onset of action, such as pain, nausea, dizziness, seizures, cardiac arrest, but also regulation of high blood pressure or of the blood sugar level.

Other suitable dosage forms comprise, for example, textile carriers, for example made of cotton or cellulose, which are saturated with a solution or suspension of the at least one pharmaceutically active ingredient.

For example, medicinal tamponades, such as those used, amongst other things, in dentistry are suitable here.

Clove oil or its main component eugenol, lavender oil or its main component linalool, methyl salicylate or ethanolic mixtures with glycerine and limonene are suitable solvents here.

Clove oils comprise the clove flower oil, the clove leaf oil and the clove style oil and are generally obtained by steam distillation from the various plant parts of the clove tree, *Syzygium aromaticum* (Myrtaceae).

Suitable active ingredient amounts that are present in such textile carriers are, for example, 50 g per 100 g of textile carrier.

Since the mucosa is a very hydrophilic permeation barrier (it is more than 90% water), the active ingredients to be applied there should be at least easily dissolved in water and thus generally more hydrophilic than lipophilic. This can be achieved for example by the administration of pharmaceutically acceptable salts of active pharmaceutical ingredients. For example, hydrochlorides of the opioid bases fentanyl and buprenorphine, which are easily dissolved in water and can be used instead of the bases themselves, especially for the treatment of breakthrough pain, can be noted here.

However, corresponding hydrophilic salts do not exist for all covalent and lipophilic medicaments. Such medicaments, such as riociguat for the treatment of pulmonary hypertension or tetrahydrocannabinol (THC) for the treatment of pain, therefore cannot be mucosally absorbed in sufficient quantity.

This absorption path is normally also closed by active ingredients having a molecular weight>300 g/mol or >1000 g/mol, such as proteins, like insulin, in spite of sufficient water solubility.

In order to nevertheless provide these active ingredients in sufficient therapeutically effective quantity, it is advantageous to reduce the permeation barrier of the mucosa temporarily and reversibly.

The aim of the invention was therefore to provide a way of temporarily and reversibly reducing the permeation barrier of the mucosa in order to thus improve an advantageous absorption of pharmaceutically active ingredients, especially of lipophilic pharmaceutically active ingredients, especially with a log P of greater than 3 or pharmaceutically active ingredients with a molecular weight>300 g/mol.

This aim is addressed in accordance with the invention by a kit comprising at least one microneedle system and at least one dosage form for transmucosally administering at least one pharmaceutically active ingredient, especially an oral thin film, comprising at least one matrix polymer and at least one pharmaceutically active ingredient.

The use of microneedles has the advantage that the permeation barrier of the mucosa is temporarily and reversibly lowered and thus allow an advantageous absorption of pharmaceutically active ingredients, especially of lipophilic pharmaceutically active ingredients, preferably with a log P of greater than 3 or pharmaceutically active ingredients with a molecular weight>300 g/mol.

In the following description of the invention, the term “comprising” can also mean “consisting of”.

The term “microneedles” shall be understood to mean needles, preferably made of a hard material, with a length from 5 to 1000 μm. The ratio of length to diameter is preferably 5:1 to 1000:1.

The kit according to the invention is preferably characterised in that the at least one dosage form for transmucosal administration comprises an oral thin film, the oral thin film comprising a matrix polymer and at least one pharmaceutically active ingredient.

The oral thin film can be of single-layer or multi-layer design.

The kit according to the invention is preferably characterised in that the at least one matrix polymer comprises a water-soluble and/or water-swellable polymer.

Water-soluble and/or water-swellable polymers comprise chemically very different natural or synthetic polymers, the common feature of which is their solubility or swellability in water or aqueous media.

The kit according to the invention is preferably characterised in that the at least one matrix polymer is selected from the group consisting of starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohols, poly(lactide-co-glycolide), hyaluronic acid, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan and natural gums, although this group is not exhaustive.

Hyaluronic acid, cellulose derivatives, alginates and/or poly(lactide-co-glycolide) are especially preferred, since the polymers are of biological origin and should therefore be pharmaceutically acceptable.

The at least one pharmaceutically active ingredient contained in the oral thin film according to the invention is not, in principle, subject to any limitation.

The kit according to the invention, however, is preferably characterised in that the at least one pharmaceutically active ingredient comprises a pharmaceutically active ingredient with a log P≥3 and/or with a molecular weight of more than 300 g/mol.

The kit according to the invention is also preferably characterised in that the at least one pharmaceutically active ingredient has a log P>2, preferably greater than 2.2 or 2.4 or 2.6 or 2.8 or 3.0 or 3.2 or 3.4 or 3.6 or 3.8 or 4 or 4.2 or 4.4 or 4.6 or 4.8 or 5 or 6 or 7.

The n-octanol-water partition coefficient $K_{ow}$ (notations such as octanol/water partition coefficient are also common and correct) is a dimensionless partition coefficient known to a person skilled in the art which indicates the ratio of the concentrations of a chemical in a two-phase system of n-octanol and water and is thus a measure of the hydrophobicity or hydrophilicity of a substance. The log P value is the decadic logarithm of the n-octanol-water partition coefficient $K_{ow}$. The following is true:

$$K_{ow} = P = \frac{c_0^{Si}}{c_w^{Si}} \text{ and } \log P = \log\frac{c_0^{Si}}{c_w^{Si}} = \log c_o^{Si} - c_w^{Si},$$

with $c_o^{Si}$=concentration of a chemical in the octanol-rich phase and $c_w^{Si}$=concentration of a chemical in the water-rich phase.

$K_{ow}$ is greater than one if a substance is more soluble in fat-like solvents such as n-octanol and less than one if it is more soluble in water. Accordingly, log P is positive for lipophilic substances and negative for hydrophilic substances.

The at least one pharmaceutically active ingredient preferably has a molecular weight of more than 300 g/mol or more than 1000 g/mol, preferably of more than 1500 g/mol or of more than 2000 g/mol, especially of more than 2500 g/mol or of more than 3000 g/mol or of more than 3500 g/mol or of more than 4000 g/mol or of more than 4500 g/mol or of more than 5000 g/mol The kit according to the invention is preferably characterised in that the at least one pharmaceutically active ingredient has a water solubility of less than 1.0 mg/ml, preferably of less than 0.5 mg/ml, or 0.1 mg/ml, or 0.05 mg/ml, or 0.001 mg/ml (at 20° C.).

The at least one pharmaceutically active ingredient in the kit according to the invention is preferably selected from the group consisting of hypnotics, sedatives, antiepileptics, analeptics, psychoneurotropic drugs, neuroleptics, neuromuscle blockers, antispasmodics, antihistamines, antiallergics, cardiotonics, antiarrhythmics, diuretics, hypotensives, vasopressors, antitussives, expectorants, analgesics, thyroid hormones, sexual hormones, glucocorticoid hormones, antidiabetics, antitumour drugs, antibiotics, chemotherapeutics, narcotics, anti-Parkinson drugs, anti-Alzheimer drugs and/or triptans, although this group is not exhaustive.

The at least one pharmaceutically active ingredient preferably comprises riociguat, tetrahydrocannabinol, cannabidiol, dronabinol, thyroid hormones and/or insulin, since, thus far, these active ingredients have been unable to find a successful parenteral administration route.

The at least one pharmaceutically active ingredient preferably comprises an active ingredient from the group of emergency medicaments. These emergency medicaments are preferably selected from the group comprising adrenalin, amiodarone, antidiuretic hormone, apomorphine, atropine, hyoscine butylbromide, clonazepam, dantrolene, dexamethasone, diazepam, entolimod, etomidate, flumazenil, furosemide, glucagon, glucocorticoids, glucose, haloperidol, heparin, ketamine, levosalbutamol, lidocaine, lorazepam, metoprolol, midazolam, morphine, naloxone, nitroglycerine, obidoxime chloride, orciprenaline, organic nitrates, propofol, salbutamol, terbutaline, theophylline, tocolytics, trimedoxime bromide and/or urapidil.

The amount of active ingredient in the oral thin film is dependent on its type and is usually 0.01 to 70 wt. %, preferably 0.1 to 50 wt. %, especially preferably 1 to 40 wt. %, in relation to the total weight of the oral thin film.

It may be advantageous if the oral thin film additionally also contains at least one auxiliary, selected from the group comprising dyes, flavourings, sweeteners, taste-masking agents, surfactants, enhancers, pH regulators, preservatives, antioxidants and/or plasticisers.

These auxiliaries are preferably each contained in the oral thin film in an amount from 0.001 to 20 wt. %.

The area density of the oral thin film is preferably 40 to 300 $g/m^2$, especially preferably 100 to 250 $g/m^2$.

The production of such an oral thin film is known to a person skilled in the art. Suitable production methods include the dissolution or dispersion of the at least one pharmaceutically active ingredient and of the at least one matrix polymer in a suitable solvent or dispersant, respectively, and the subsequent spreading and drying of this solution or dispersion in order to obtain an oral thin film.

A microneedle system, also called a microneedle array, preferably comprises a system comprising a plurality of microneedles on a carrier. The needles, which preferably have a length of 5 μm to 1000 μm, can be made of different materials such as ceramic, steel, polymers or $SiO_2$.

The kit according to the invention is preferably characterised in that the microneedle system is a microneedle system based on glass, $SiO_2$, steel, ceramic, starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohols, poly(lactide-co-glycolide), hyaluronic acid, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan and natural gums, although this group is not exhaustive.

Microneedle systems based on hyaluronic acid, cellulose derivatives, alginates and/or poly(lactide-co-glycolide) are especially preferred here, since the polymers are of biological origin and should therefore be pharmaceutically acceptable (apart from specific allergic reactions to these substances).

Suitable microneedle systems are known to a person skilled in the art and are described for example in U.S. Pat. Nos. 7,658,728, 7,785,301 or 8,414,548, the content of which is hereby incorporated across its full scope. Suitable microneedle systems are obtainable for example under the trade names "AdminPatch" by the company "nanobioSciences" (CA, USA).

The kit according to the invention is preferably characterised in that the microneedle system has microneedles with a length from 100 μm to 600 μm, preferably from 250 μm to 350 μm, especially preferably of approximately 300 μm.

The kit according to the invention is also preferably characterised in that the microneedle system has 30 to 400, preferably 200 to 250 microneedles per $cm^2$.

The kit according to the invention is preferably characterised in another embodiment in that the microneedle system has 39 microneedles per $cm^2$.

The present invention further relates to the kit according to the invention, as described above, for use in treating a patient.

The present invention also relates to the use of a microneedle system, as described above, for reducing or decreasing the permeation barrier of a mucosa for at least one pharmaceutically active ingredient.

According to this use, a mucosa comprises especially the human oral mucosa.

The at least one pharmaceutically active ingredient in accordance with this use is to be understood here as defined above.

The present invention also relates to a method for treating a patient comprising the steps of a) applying a microneedle system to a point of a mucosa of a patient,
b) removing the microneedle system, and
c) applying an oral thin film, comprising at least one matrix polymer and at least one pharmaceutically active ingredient, to the point of the mucosa where the microneedle system was applied in step a) and removed again instep b).

The mucosa preferably comprises the human oral mucosa.

The microneedle system and the at least one pharmaceutically active ingredient are to be understood as defined above.

The microneedle system is preferably pressed with a pressure from 1 to 5N, preferably approximately 3N, onto the mucosa of the patient.

The contact time is preferably 2 to 20 sec, especially preferably 5 to 15 sec, and especially approximately 10 sec.

The microneedle system is then removed and the oral thin film is applied to the same point preferably within 5 to 15 sec, preferably within 5 sec.

The present invention also relates to a method for treating a patient comprising the steps of a) applying a microneedle system to a point of a mucosa of a patient,
b) simultaneously applying a dosage form for transmucosally administering at least one pharmaceutically active ingredient to the side of the microneedle system which does not contact the mucosa.

The mucosa preferably comprises the human oral mucosa.

The microneedle system and the at least one pharmaceutically active ingredient are to be understood as defined above.

The microneedle system is preferably pressed with a pressure from 1 to 5N, preferably approximately 3N, onto the mucosa of the patient.

The dosage form for transmucosally administering at least one pharmaceutically active ingredient can be, for example, a textile carrier, such as a tamponade used in dentistry, which is saturated with a solution or suspension of the at least one pharmaceutically active ingredient.

The present invention also relates to a biodegradable microneedle system comprising at least one pharmaceutically active ingredient and at least one biodegradable polymer.

The use of such a biodegradable microneedle system has the advantage that the permeation barrier of the mucosa is temporarily and reversibly lowered and thus an advantageous absorption of pharmaceutically active ingredients, especially of lipophilic pharmaceutically active ingredients, preferably with a log P of greater than 3 or pharmaceutically active ingredients with a molecular weight>300 g/mol is made possible.

The term "microneedles" shall be understood to mean needles, preferably made of a hard material, with a length from 5 to 1000 μm. The ratio of length to diameter is preferably 5:1 to 1000:1.

Following the administration of the microneedle system, this dissolves in the mouth of the patient and in so doing releases the contained pharmaceutically active ingredient.

The biodegradable microneedle system according to the invention is furthermore preferably characterised in that the microneedle system has microneedles with a length from 100 μm to 500 μm, preferably from 250 μm to 350 μm, and/or has 50 to 400, preferably 200 to 250 microneedles per $cm^2$.

The biodegradable microneedle system according to the invention is also preferably characterised in that the at least one biodegradable polymer is a polymer based on sugar, hyaluron or polyvinylpyrrolidone.

The at least one pharmaceutically active ingredient contained in the biodegradable microneedle system according to the invention is not, in principle, subject to any limitation.

The biodegradable microneedle system according to the invention, however, is preferably characterised in that the at least one pharmaceutically active ingredient comprises a pharmaceutically active ingredient with a log P≥3 and/or with a molecular weight of more than 300 g/mol.

The biodegradable microneedle system according to the invention is also preferably characterised in that the at least one pharmaceutically active ingredient has a log P>2, preferably greater than 2.2 or 2.4 or 2.6 or 2.8 or 3.0 or 3.2 or 3.4 or 3.6 or 3.8 or 4 or 4.2 or 4.4 or 4.6 or 4.8 or 5 or 6 or 7.

The n-octanol-water partition coefficient $K_{ow}$ (notations such as octanol/water partition coefficient are also common and correct) is a dimensionless partition coefficient known to a person skilled in the art which indicates the ratio of the concentrations of a chemical in a two-phase system of n-octanol and water and is thus a measure of the hydrophobicity or hydrophilicity of a substance. The log P value is the decadic logarithm of the n-octanol-water partition coefficient $K_{ow}$. The following is true:

$$K_{ow} = P = \frac{c_0^{Si}}{c_w^{Si}} \text{ and } \log P = \log \frac{c_0^{Si}}{c_w^{Si}} = \log c_o^{Si} - c_w^{Si},$$

with $c_o^{Si}$=concentration of a chemical in the octanol-rich phase and $c_w^{Si}$=concentration of a chemical in the water-rich phase.

$K_{ow}$ is greater than one if a substance is more soluble in fat-like solvents such as n-octanol and less than one if it is more soluble in water. Accordingly, log P is positive for lipophilic substances and negative for hydrophilic substances.

The at least one pharmaceutically active ingredient preferably has a molecular weight of more than 300 g/mol or more than 1000 g/mol, preferably of more than 1500 g/mol or of more than 2000 g/mol, especially of more than 2500 g/mol or of more than 3000 g/mol or of more than 3500 g/mol or of more than 4000 g/mol or of more than 4500 g/mol or of more than 5000 g/mol The biodegradable microneedle system according to the invention is preferably characterised in that the at least one pharmaceutically active ingredient has a water solubility of less than 1.0 mg/ml, preferably of less than 0.5 mg/ml, or 0.1 mg/ml, or 0.05 mg/ml, or 0.001 mg/ml (at 20° C.).

The at least one pharmaceutically active ingredient is preferably not present in the form of a salt in the biodegradable microneedle system.

The at least one pharmaceutically active ingredient in the biodegradable microneedle system according to the invention is preferably selected from the group consisting of hypnotics, sedatives, antiepileptics, analeptics, psychoneurotropic drugs, neuroleptics, neuro-muscle blockers, antispasmodics, antihistamines, antiallergics, cardiotonics, antiarrhythmics, diuretics, hypotensives, vasopressors, antitussives, expectorants, analgesics, thyroid hormones, sexual hormones, glucocorticoid hormones, antidiabetics, antitumour drugs, antibiotics, chemotherapeutics, narcotics, anti-Parkinson drugs, anti-Alzheimer drugs and/or triptans, although this group is not exhaustive.

The at least one pharmaceutically active ingredient preferably comprises riociguat, tetrahydrocannabinol, cannabidiol, dronabinol, thyroid hormones, adrenalin hydrogen tartrate and/or insulin, since, thus far, these active ingredients have been unable to find a successful parenteral administration route.

The at least one pharmaceutically active ingredient preferably comprises an active ingredient from the group of emergency medicaments. These emergency medicaments are preferably selected from the group comprising adrenalin, amiodarone, antidiuretic hormone, apomorphine, atropine, hyoscine butylbromide, clonazepam, dantrolene, dexamethasone, diazepam, entolimod, etomidate, flumazenil, furosemide, glucagon, glucocorticoids, glucose, haloperidol, heparin, ketamine, levosalbutamol, lidocaine, lorazepam, metoprolol, midazolam, morphine, naloxone, nitroglycerine, obidoxime chloride, orciprenaline, organic nitrates, propofol, salbutamol, terbutaline, theophylline, tocolytics, trimedoxime bromide and/or urapidil.

The amount of active ingredient in the biodegradable microneedle system is dependent on its type and is usually 0.01 to 70 wt. %, preferably 0.1 to 50 wt. %, especially preferably 1 to 40 wt. %, in relation to the total weight of the oral thin film.

It may be advantageous if the biodegradable microneedle system additionally also contains at least one auxiliary, selected from the group comprising dyes, flavourings, sweeteners, taste-masking agents, surfactants, enhancers, pH regulators, preservatives, antioxidants and/or plasticisers.

These auxiliaries are preferably each contained in the oral thin film in an amount from 0.001 to 20 wt. %.

Eugenol is preferably provided as enhancer in the biodegradable microneedle system according to the invention.

The present invention also relates to a biodegradable microneedle system as described above for use as a medicament.

The present invention also relates to a biodegradable microneedle system as described above for use as a medicament for application to the oral mucosa of a mammal, especially for application to the human oral mucosa.

Figure 1:
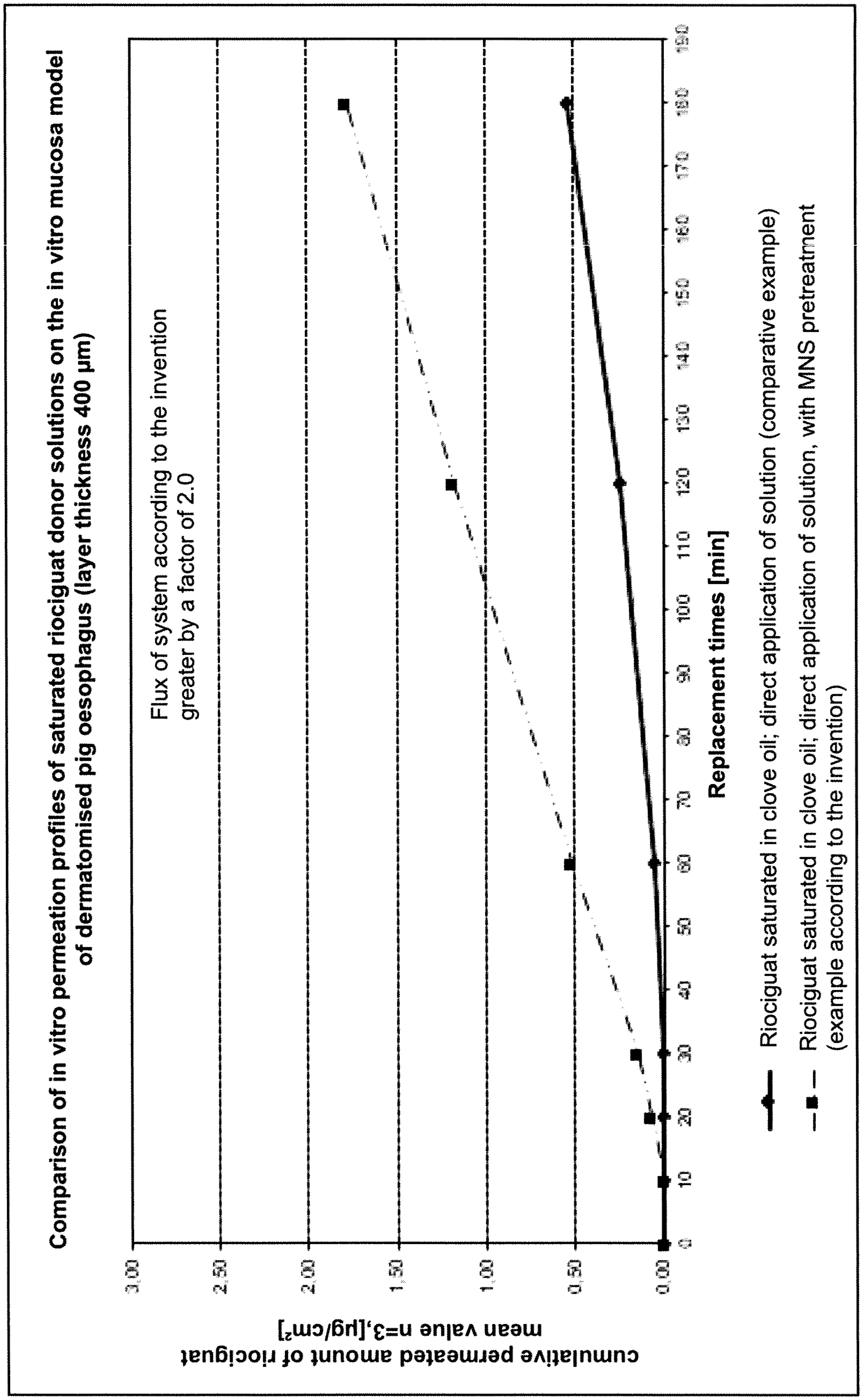
FIG. 1: Comparison of in vitro permeation profiles of a saturated riociguat solution in clove oil on the in vitro mucosa model according to Example 1. Then active ingredient flux after pretreatment with a microneedle system is higher by a factor of 2.0 in comparison to administration without pretreatment.

The invention will be explained below by means of non-limiting examples.

EXAMPLES

The following test series with the selected active ingredients in each case were performed within the scope of a typical in vitro permeation by means of Franz diffusion cells (volume 10 mL) at 37° C. The used acceptor medium was replaced completely for a new one at predetermined replacement times, and the content of permeated active ingredient amount in these acceptor solutions was determined by means of HPLC.

The used donor and acceptor media were each selected in view of the solubility of the example active ingredients.

The used donor solutions were applied for Examples 1-3 directly to the mucosa surface using pipettes. The amount of the donor solutions was 150 μl for each of example active ingredients 1, 2 and 3.

A commercial system made of steel and known under the trade name "AdminPatch™" from the company "nanobio-Sciences" (CA, USA) was used as microneedle system in Examples 1 to 4 and 10.

The contact pressure was 3 N by thumb pressure, monitored by means of a Roberval balance. The pressing time was 10 sec.

The length of the microneedles in Examples 1 to 4 and 10 was 600 μm in each case. A total of 187 microneedles were applied to an area of 0.785 $cm^2$ (microneedle density=238 per $cm^2$).

For Example 4, the donor solution was injected (900 μl) onto or into the used dentistry tamponade (length and diameter 1 cm each). The microneedle system was fixed to the underside of the tamponade and was applied to the mucosa surface perpendicularly through the head of the Franz cells and fixed in a defined position by a suitable stopper and with moderate pressure.

In Examples 5 to 9 biodegradable microneedle systems loaded with active ingredient were examined by means of Franz diffusion cells, as described above.

In Example 10 an active-ingredient-containing oral thin film was applied to the pretreated mucosa surface similarly to Examples 1 to 3 using the "AdminPatch™" microneedle system (needle length 600 μm).

The results of the permeation studies with the different active ingredients are shown in FIGS. 1 to 10.

Example 1

Permeation Study with Riociguat

Phosphate buffer (pH 5.5) was used as acceptor medium and an addition of 2 wt. % Tween® 20 was used as organic solvent to maintain "sink" conditions. (sink=current solubility at time t of an active ingredient in an acceptor medium of at most 30% of its saturation solubility in this acceptor medium)

A saturated solution of riociguat in clove oil (Primavera® clove bud organic essential oil, Oy-Mittelberg, Germany) was used as donor solution.

Dermatomised skin from the oesophagus of a pig with a layer thickness of 400 μm was used as skin model.

The results of the permeation study are shown in FIG. 1.

Example 2

Permeation Study with Human Insulin 0.025 molar HEPES buffer (pH 7.4) was used as acceptor medium.

A saturated solution of human insulin in natural human saliva was used as donor solution.

Dermatomised skin from the oesophagus of a pig with a layer thickness of 400 μm was used as skin model.

Figure 2:
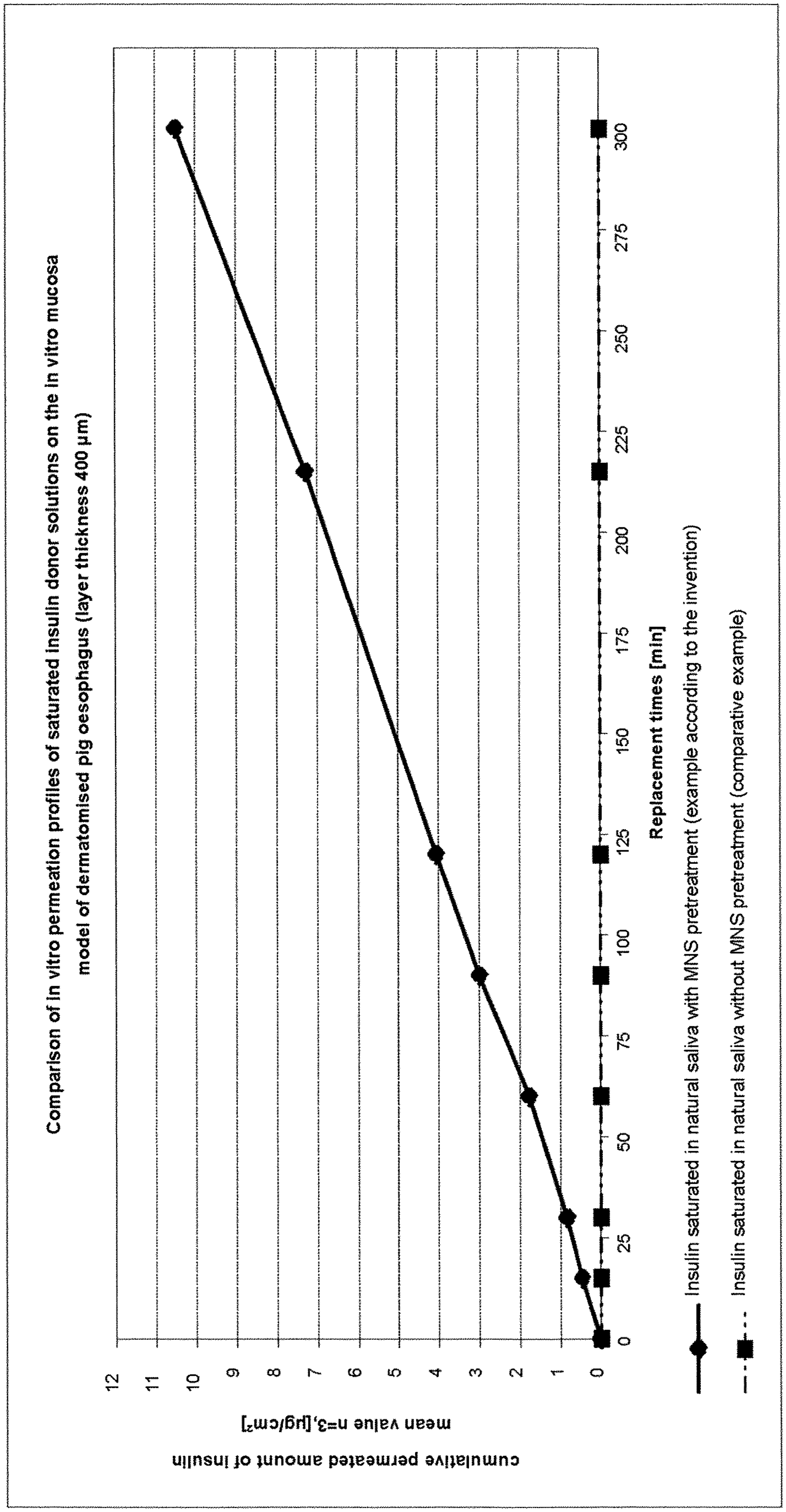
FIG. 2: Comparison of in vitro permeation profiles of a saturated human insulin solution in natural human saliva on the in vitro mucosa model according to Example 2. An active ingredient flux could be observed only after pretreatment with a microneedle system. It was not possible to detect any permeated active ingredient without pretreatment.

The results of the permeation study are shown in FIG. 2.

Example 3

Permeation Study with Tetrahydrocannabinol (THC)

Phosphate buffer (pH 5.5) was used as acceptor medium and an addition of 2 wt. % Tween® 20 was used as organic solvent to maintain “sink” conditions.

A saturated solution of tetrahydrocannabinol in clove oil (Primavera® clove bud organic essential oil, Oy-Mittelberg, Germany) was used as donor solution.

Dermatomised skin from the oesophagus of a pig with a layer thickness of 400 μm was used as skin model.

Figure 3:
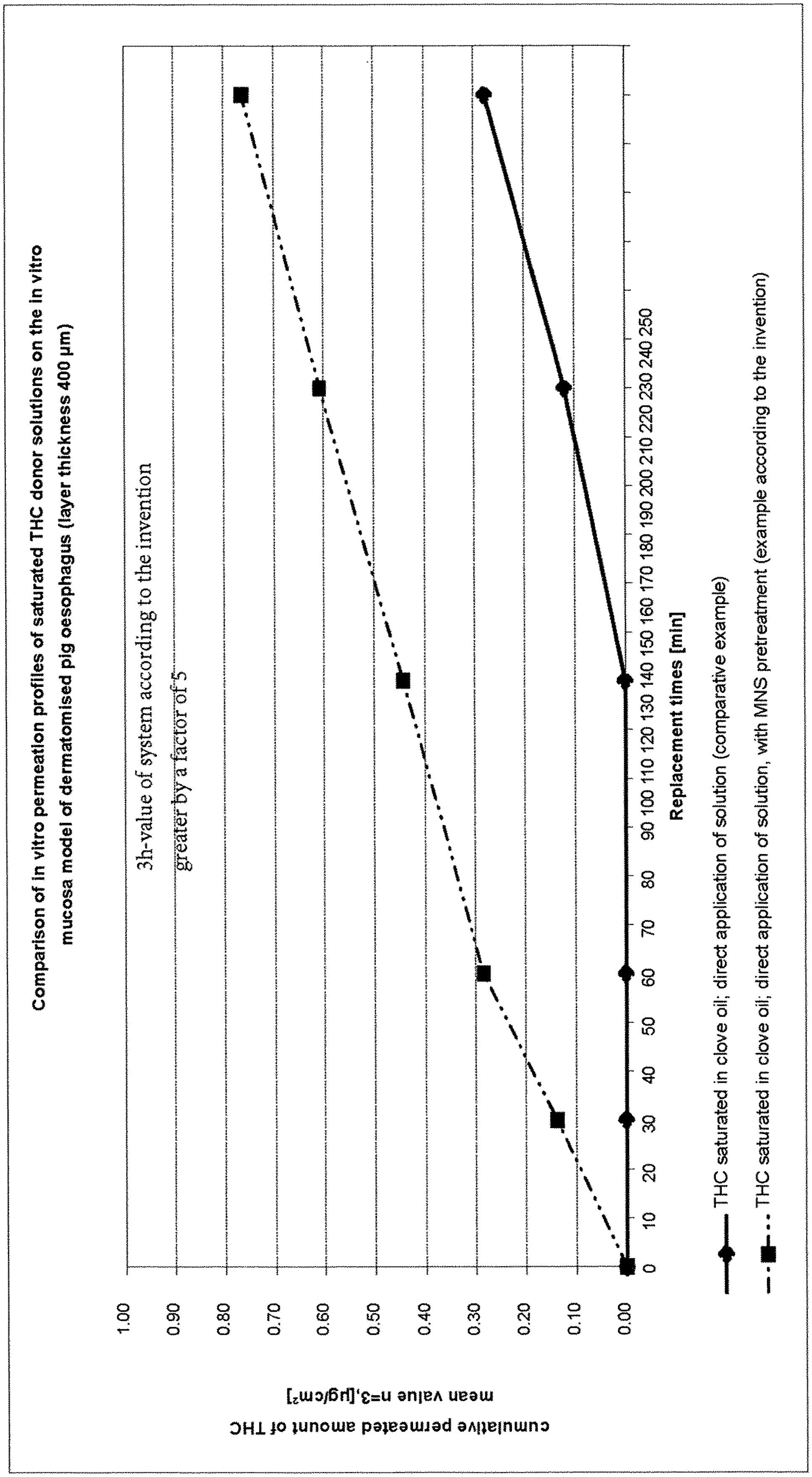
FIG. 3: Comparison of in vitro permeation profiles of a saturated tetrahydrocannabinol solution in clove oil on the in vitro mucosa model according to Example 3. Without pretreatment, permeated active ingredient could only be detected after 3 hours. This value was lower by a factor of 5 in comparison to pretreated mucosa.

The results of the permeation study are shown in FIG. 3.

Example 4

Permeation Study with Cannabidiol (CBD)

Phosphate buffer (pH 5.5) was used as acceptor medium and an addition of 2 wt. % Tween® 20 was used as organic solvent to maintain “sink” conditions.

A saturated solution of tetrahydrocannabinol in clove oil (Primavera® clove bud organic essential oil, Oy-Mittelberg, Germany) was used as donor solution.

Dermatomised skin from the oesophagus of a pig with a layer thickness of 400 μm was used as skin model.

Figure 4:
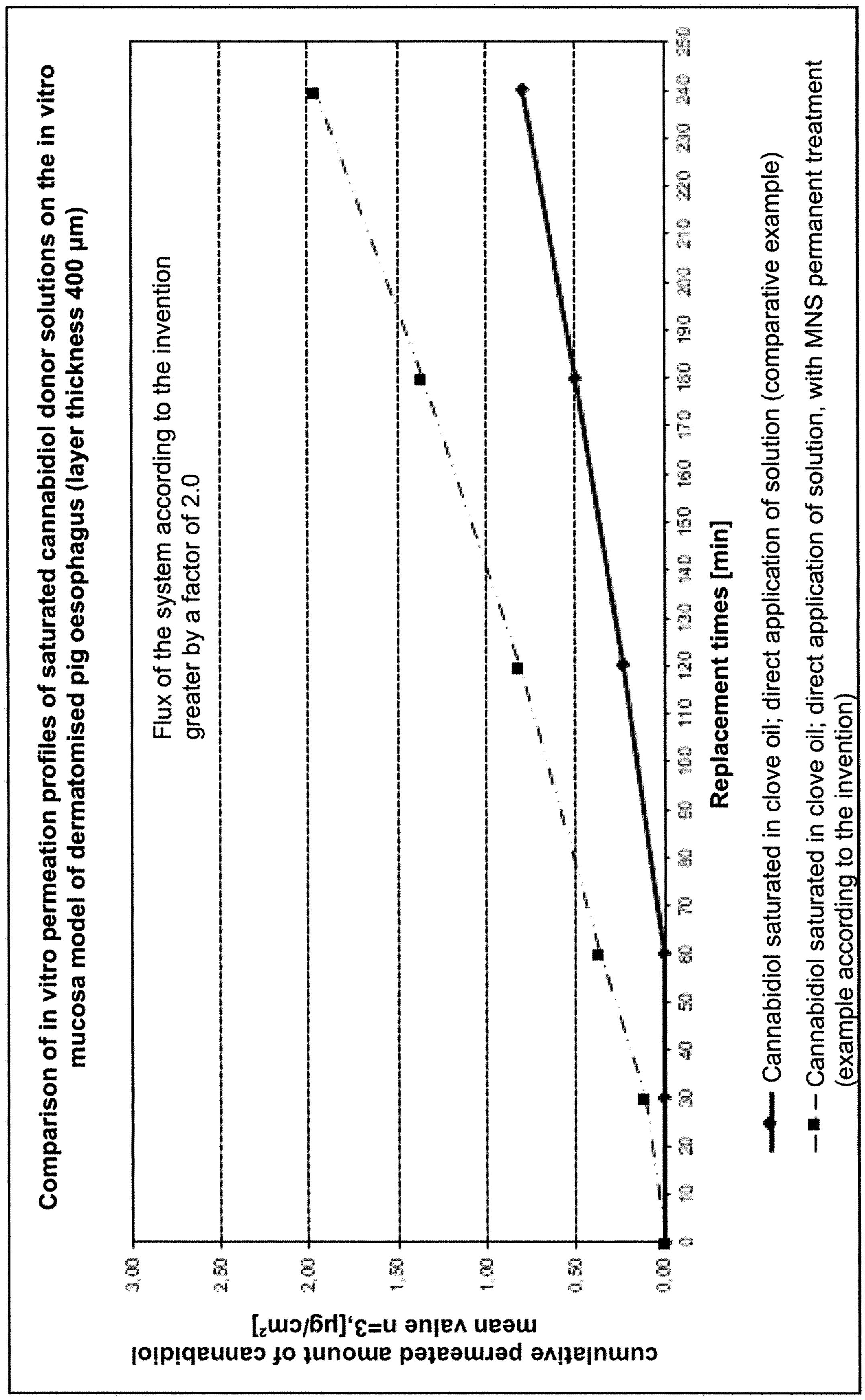
FIG. 4: Comparison of in vitro permeation profiles of a saturated cannabidiol solution in clove oil on the in vitro mucosa model according to Example 3. The active ingredient flux after pretreatment with a microneedle system is higher by a factor of 2.0 in comparison to administration without pretreatment.

The results of the permeation study are shown in FIG. 4.

Example 5

Permeation Study with Sumatriptan Succinate

Phosphate buffer (pH 7.4) without further additives was used as acceptor medium; sumatriptan succinate as water-soluble salt is very easily dissolved in this acceptor.

The donor system was a polyvinylpyrrolidone-based microneedle system which was loaded with sumatriptan succinate and which dissolves upon contact with water and at temperatures≥32° C.

For preparation, sumatriptan succinate, polyvinylpyrrolidone, Polysorbate 80 and glycerol were dissolved in water with the proportions 5:20:1:1:73 (in each case in wt. %). The finished solution was poured into negative needle moulds made of silicone, the surface of which was coated with a thin platinum layer by vacuum metallisation. The negative moulds were then dried overnight at room temperature. The dried microneedle systems were carefully pressed out from the dies after the drying process and stored under exclusion of moisture until their further use. The active ingredient content was 4.25 mg sumatriptan succinate per 0.785 $cm^2$ of system or 5.41 $mg/cm^2$.

The length of the microneedles of the used microneedle system was 500 μm. A total of 600 microneedles were applied to an area of 0.785 $cm^2$ (microneedle density=764 per $cm^2$).

Dermatomised skin from the oesophagus of a pig with a layer thickness of 400 μm was used as skin model.

The microneedle system remained in the mucosa throughout the permeation period, the cell head additionally also having been filled with lead balls in order to simulate the in vivo contact pressure (for example between mandible and oral mucosa) in the oral cavity. As protection for the dissolving microneedle system, a separation film based on siliconised PET (polyethylene terephthalate) was also introduced in between in front of the lead balls.

Figure 5:
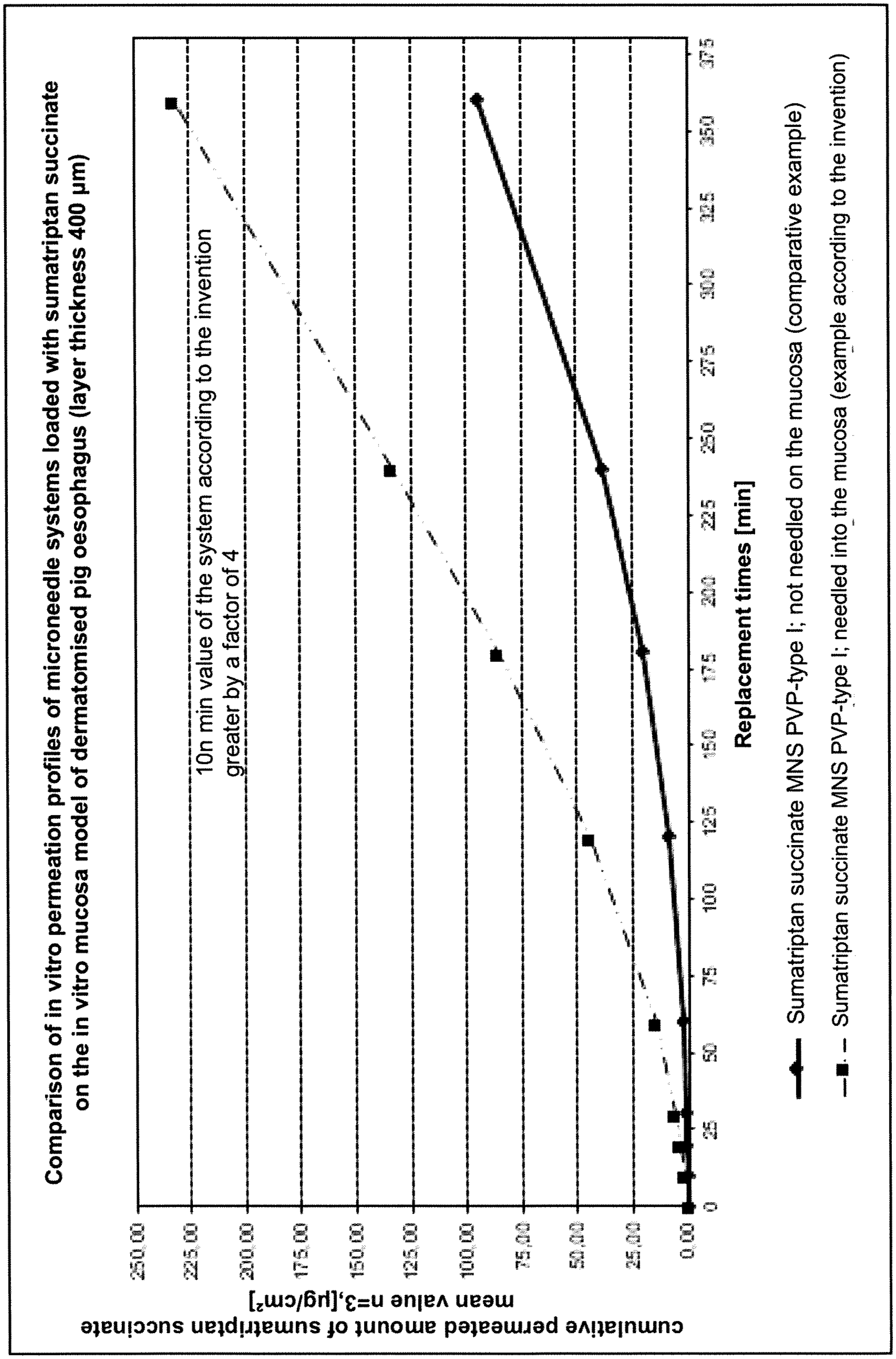
FIG. 5: Comparison of in vitro permeation profiles of a dissolving microneedle system applied directly into the mucosa and loaded with sumatriptan succinate on the in vitro mucosa model according to Example 5. The comparative example was the same system, but applied in reverse, i.e. with the needle side upward not penetrating into the mucosa. In order to simulate the in vivo contact pressure in the oral cavity, the microneedle systems were weighted from above with lead balls as weights, both in the comparative example and in the example according to the invention. The active ingredient flux with the microneedle system applied in the mucosa is higher by a factor of 2.0 in comparison to the system without penetration into the mucosa. The first permeation value after 10 min for the example according to the invention is higher by a factor of approximately 4 in comparison to the comparative example.

The results of the permeation study are shown in FIG. 5.

Example 6

Permeation Study with Adrenalin Hydrogen Tartrate

Phosphate buffer (pH 6.0) with 0.1 wt. % L-ascorbic acid was used as acceptor medium; adrenalin hydrogen tartrate is very easily dissolved in this acceptor.

The biodegradable microneedle system was prepared and applied similarly to Example 5, with adrenalin hydrogen tartrate having been used as pharmaceutically active ingredient.

Figure 6:
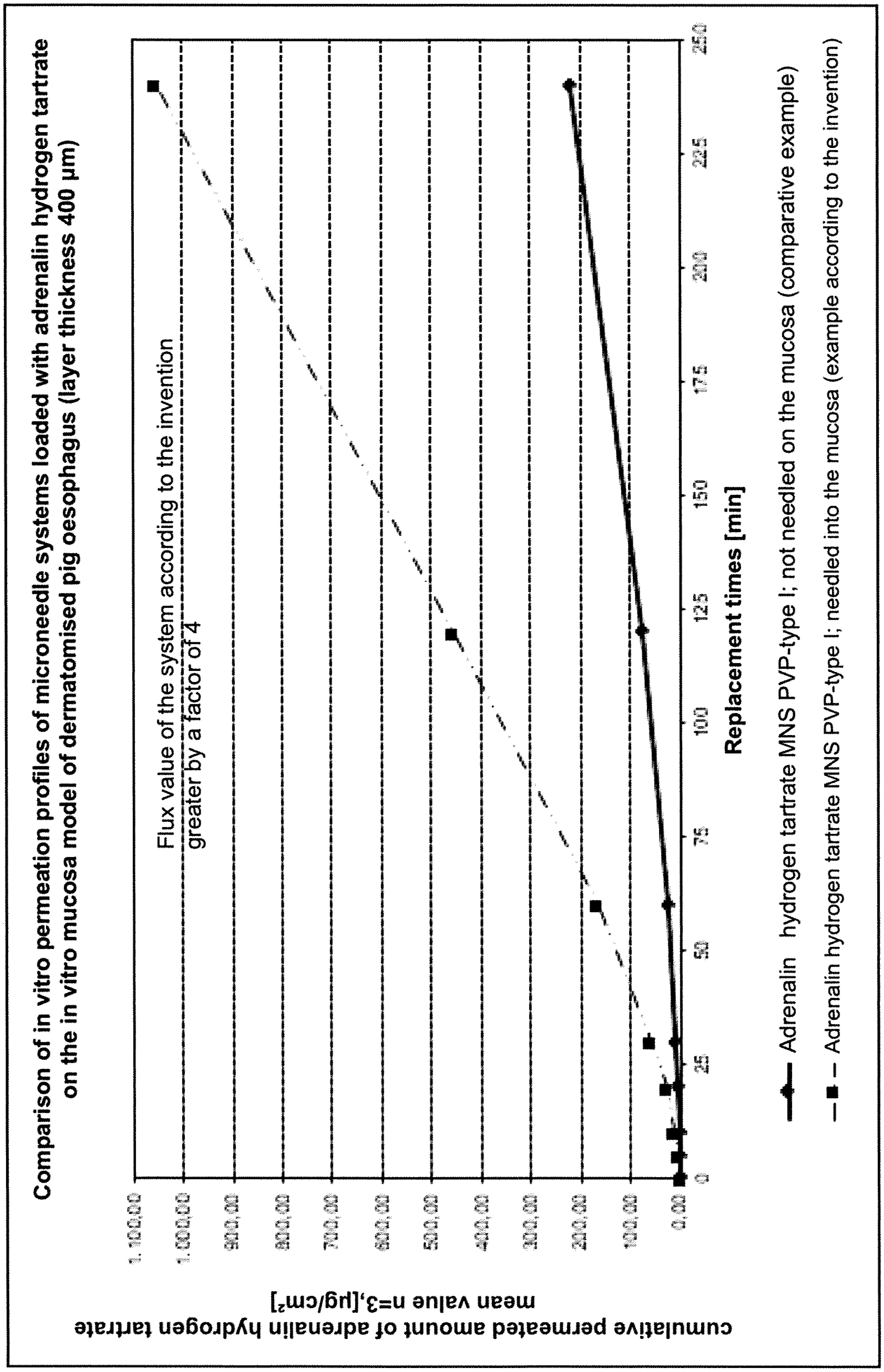
FIG. 6: Comparison of in vitro permeation profiles of a dissolving microneedle system applied directly into the mucosa and loaded with adrenalin hydrogen tartrate on the in vitro mucosa model according to Example 6. The comparative example was the same system, but applied in reverse, i.e. with the needle side upward not penetrating into the mucosa. In order to simulate the in vivo contact pressure in the oral cavity, the microneedle systems were weighted from above with lead balls as weights, both in the comparative example and in the example according to the invention. The active ingredient flux with the microneedle system applied in the mucosa is higher by a factor of 4 in comparison to the system without penetration into the mucosa.

The results of the permeation study are shown in FIG. 6.

Example 7

Permeation Study with Salbutamol Sulphate

Phosphate buffer (pH 7.4) without further additives was used as acceptor medium; salbutamol sulphate is very easily dissolved in this acceptor.

The biodegradable microneedle system was prepared and applied similarly to Example 5, with salbutamol sulphate having been used as pharmaceutically active ingredient.

Figure 7:
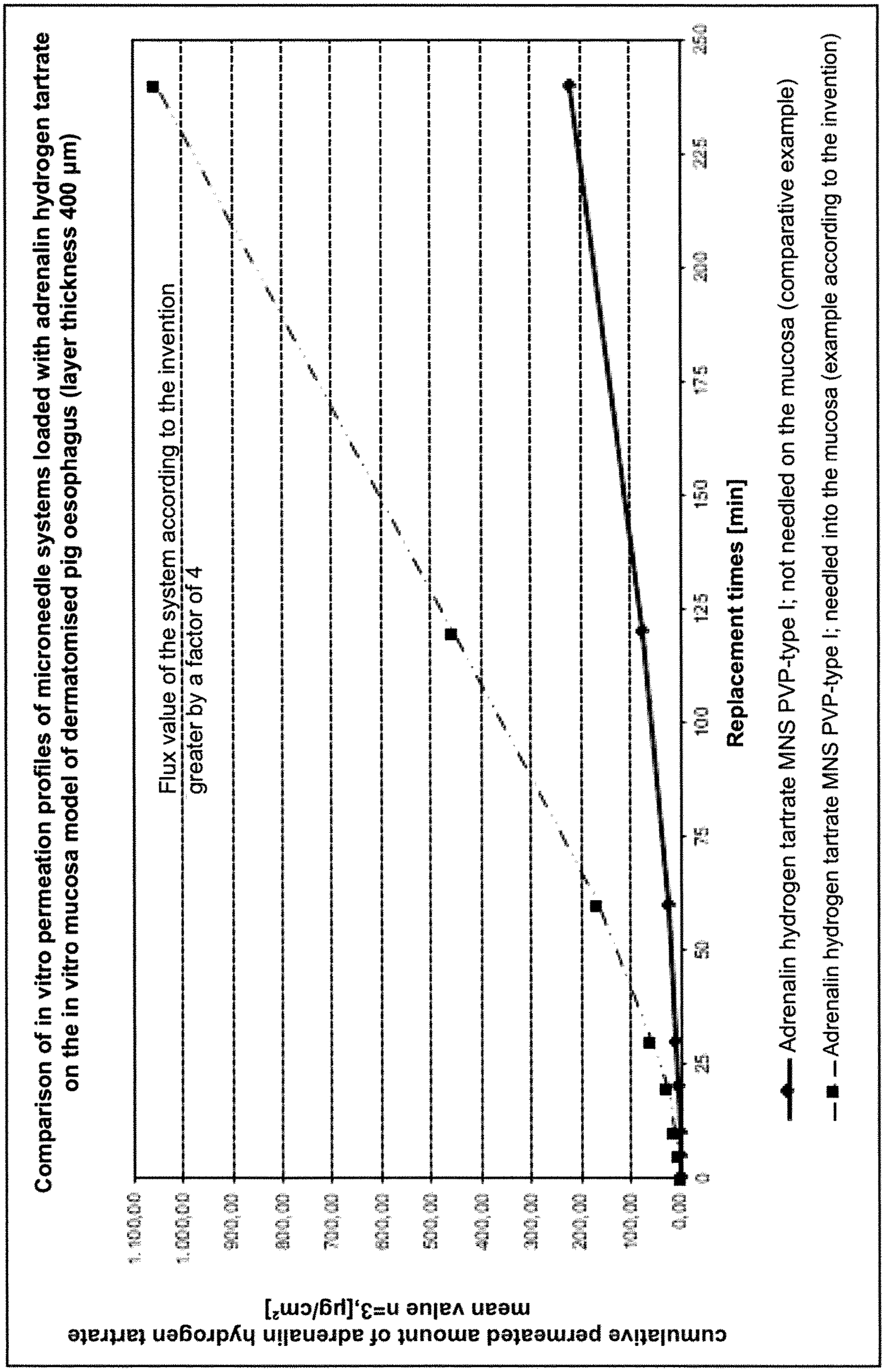
FIG. 7: Comparison of in vitro permeation profiles of a dissolving microneedle system applied directly into the mucosa and loaded with salbutamol sulphate on the in vitro mucosa model according to Example 7. The comparative example was the same system, but applied in reverse, i.e. with the needle side upward not penetrating into the mucosa. In order to simulate the in vivo contact pressure in the oral cavity, the microneedle systems were weighted from above with lead balls as weights, both in the comparative example and in the example according to the invention. The active ingredient flux with the microneedle system applied in the mucosa is higher by a factor of 2 in comparison to the system without penetration into the mucosa.

The results of the permeation study are shown in FIG. 7.

Example 8

Permeation Study with Apomorphine Hydrochloride

Phosphate buffer (pH 6.8) with 0.1 wt. % L-ascorbic acid was used as acceptor medium; apomorphine hydrochloride is very easily dissolved in this acceptor.

The biodegradable microneedle system was prepared similarly to Example 5, with apomorphine hydrochloride having been used as pharmaceutically active ingredient.

Figure 8:
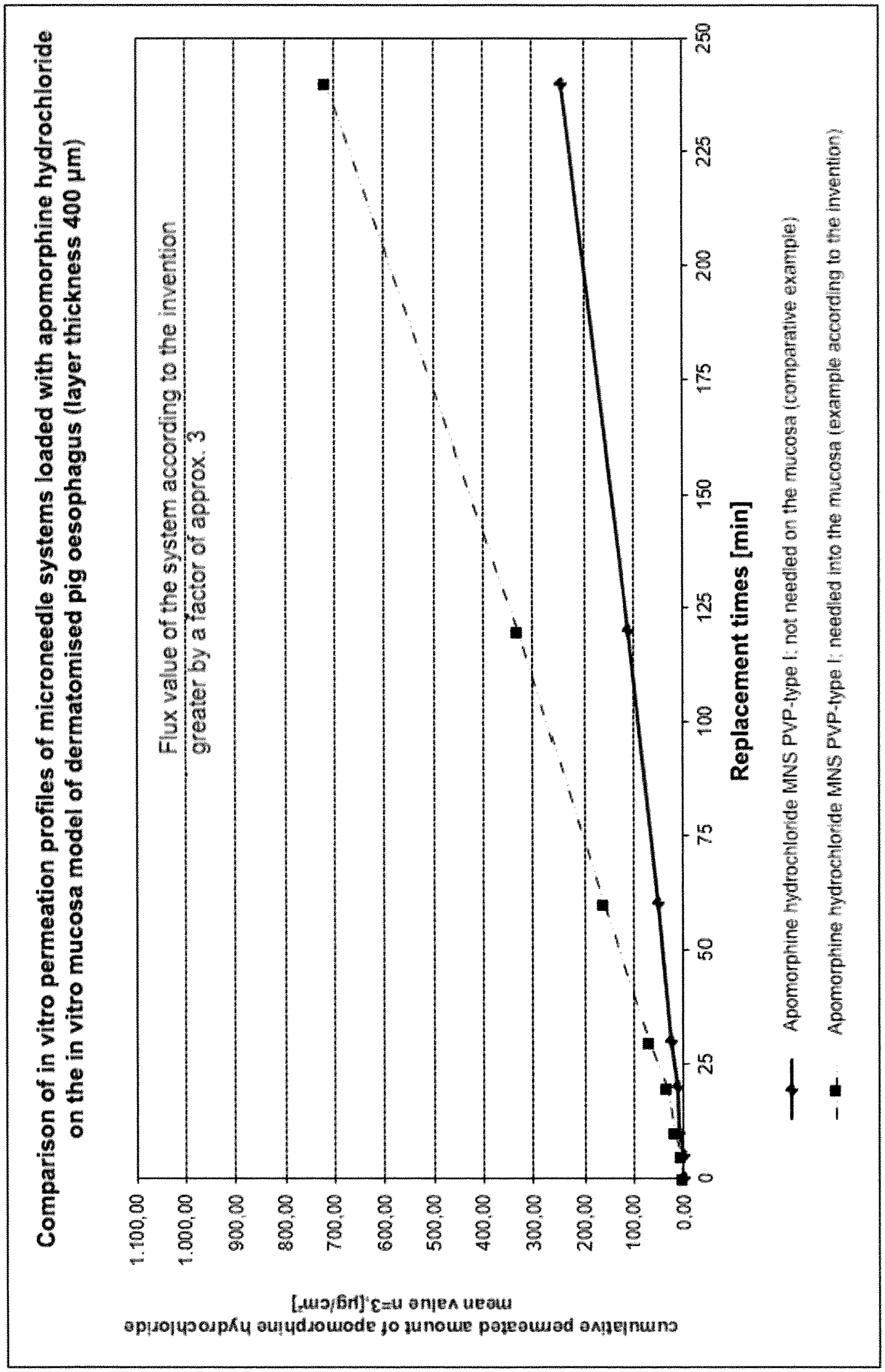
FIG. 8: Comparison of in vitro permeation profiles of a dissolving microneedle system applied directly into the mucosa and loaded with apomorphine hydrochloride on the in vitro mucosa model according to Example 8. The comparative example was the same system, but applied in reverse, i.e. with the needle side upward not penetrating into the mucosa. In order to simulate the in vivo contact pressure in the oral cavity, the microneedle systems were weighted from above with lead balls as weights, both in the comparative example and in the example according to the invention. The active ingredient flux with the microneedle system applied in the mucosa is higher by a factor of 3 in comparison to the system without penetration into the mucosa.

The results of the permeation study are shown in FIG. 8.

Example 9

Permeation Study with Sumatriptan Base

Phosphate buffer (pH 6.0) with 2 wt. % Tween 20 was used as acceptor medium; sumatriptan base is very easily dissolved in this acceptor.

The biodegradable microneedle system was prepared and applied similarly to Example 5, with sumatriptan base having been used as pharmaceutically active ingredient.

Figure 9:
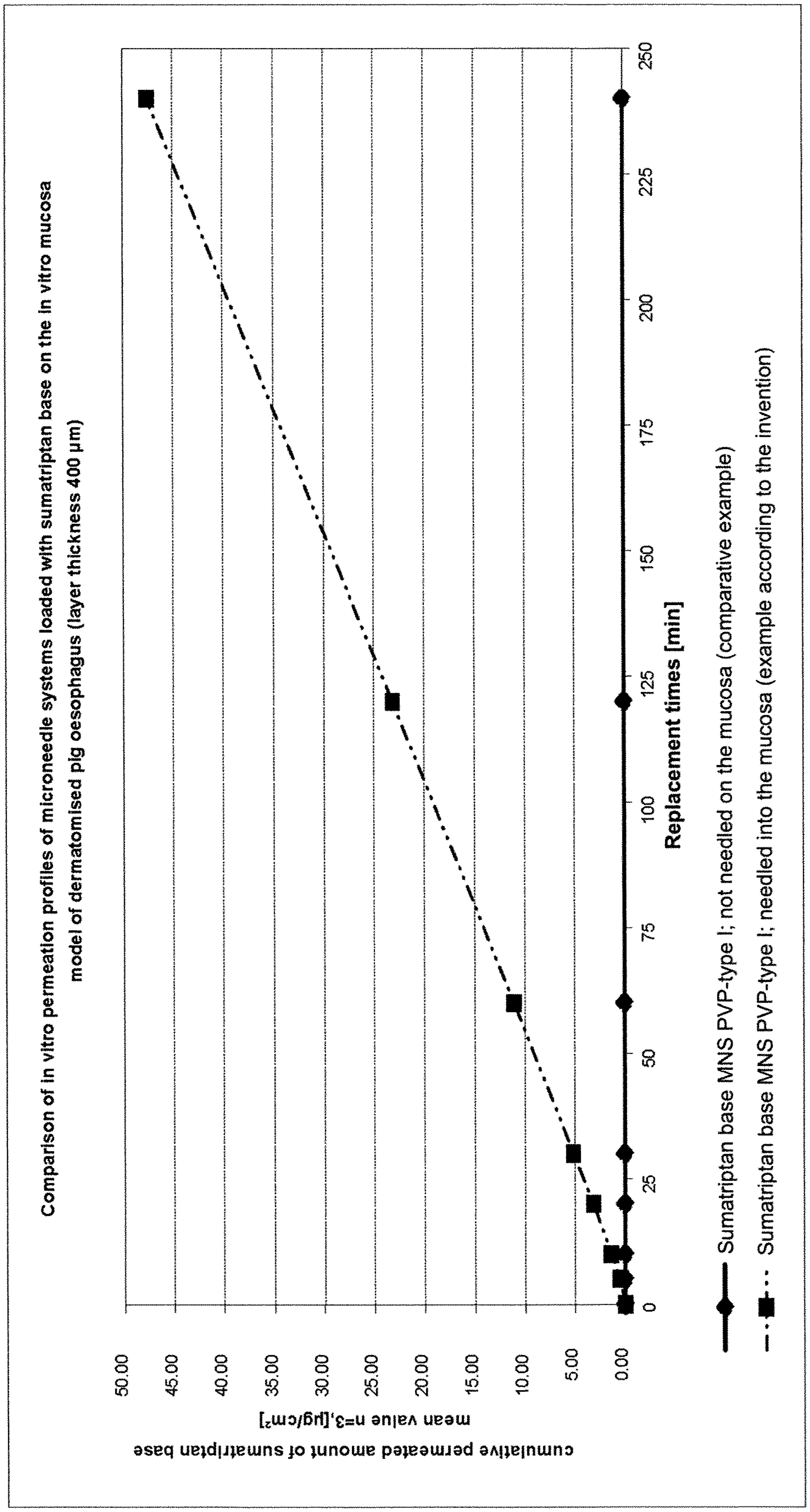
FIG. 9: Comparison of in vitro permeation profiles of a dissolving microneedle system applied directly into the mucosa and loaded with sumatriptan base on the in vitro mucosa model according to Example 9. The comparative example was the same system, but applied in reverse, i.e. with the needle side upward not penetrating into the mucosa. In order to simulate the in vivo contact pressure in the oral cavity, the microneedle systems were weighted from above with lead balls as weights, both in the comparative example and in the example according to the invention. It was not possible to measure an active ingredient flux in the comparative example. By contrast, a high active ingredient flux could be observed in the microneedle system applied in the mucosa.

The results of the permeation study are shown in FIG. 9.

Example 10

The oral thin film was produced as follows:

1) the active ingredient (25 g) was weighed into and suspended in water (50 g) with stirring (1 h at 1200 rpm),
2) the further constituents were added successively and in portions, 60 g hydroxypropyl methylcellulose, 15 g glycerol, 3 g Na saccharin, with stirring,
3) the batch was stored overnight in a fridge,
4) the batch was homogenised using an UltraTurrax device for 5 min at 1350 rpm,
5) the batch was stored once more overnight in a fridge,
6) a thin film (layer thickness 800 μm) was removed using a sheeting-out doctor blade (Erichsen® hand-held doctor blade) onto the non-siliconised side of laminated paper 1200 μm thick,
7) the removed film was dried for 10 min at room temperature and then for 20 min at 70° C. in a circulating-air drying oven, and
8) circular blanks (diameter 25 cm) were punched out from the film and sealed in four-side sealed pouches.

The oral thin film had the following composition (in wt. %):

25% active ingredient ulipristal acetate

60% polymer consisting of hydroxypropyl methyl cellulose

12% glycerol

3% Na saccharin

Phosphate buffer (pH 7.4) with 2 wt. % Tween 20 was used as acceptor medium; ulipristal acetate is very easily dissolved in this acceptor.

The surface of the mucosa was treated with the "AdminPatch™" microneedle system (needle length 600 μm) from the company "nanobioSciences" (CA, USA) made of steel with a contact pressure of 3 N by thumb pressure, monitored by means of a Roberval balance for 10 sec.

Immediately thereafter, the oral thin film was applied, preferably with the simultaneous addition of 100 μl Glandosane®, to start dissolving the oral thin film.

Oral thin films should always start the dissolution process as quasi-solid substances so to speak. The agent used here to start dissolution should preferably simulate the naturally produced saliva which causes the oral thin film to dissolve or at least start to dissolve in vivo. In the present case, Glandosane® was used for reasons of improved solubility. Glandosane® (artificial saliva) is a spray to be applied in the oral cavity for xerostomia and for oral care on intensive care wards.

Figure 10:
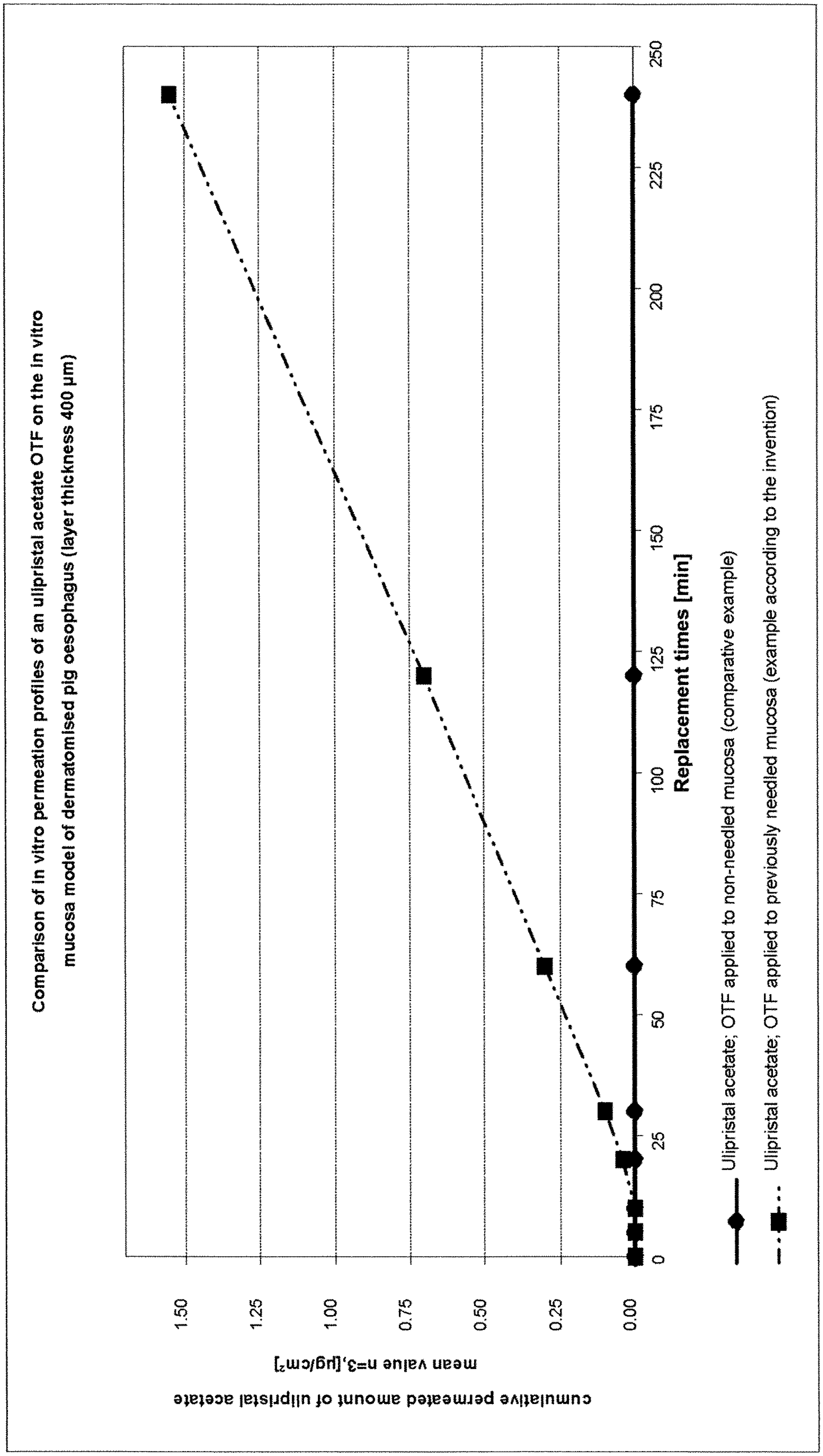
FIG. 10: Comparison of in vitro permeation profiles of an ulipristal acetate-containing oral thin film on the in vitro mucosa model according to Example 10. An active ingredient flux could be observed only after pretreatment with a microneedle system. It was not possible to detect any permeated active ingredient without pretreatment.

The results of the permeation study are shown in FIG. 10.

The invention claimed is:

1. A kit, comprising at least one microneedle system and at least one dosage form for transmucosally administering at least one pharmaceutically active ingredient, wherein the at least one dosage form comprises an oral thin film comprising at least one matrix polymer and at least one pharmaceutically active ingredient, wherein the at least one matrix polymer comprises a water-soluble and/or water-swellable polymer.

2. The kit according to claim 1, wherein the at least one pharmaceutically active ingredient comprises a pharmaceutically active ingredient with a log P≥3.

3. The kit according to claim 1, wherein the at least one pharmaceutically active ingredient comprises a pharmaceutically active ingredient with a molecular weight of greater than 300 g/mol.

4. The kit according to claim 1, wherein the at least one pharmaceutically active ingredient is selected from the group consisting of hypnotics, sedatives, antiepileptics, analeptics, psychoneurotropic drugs, neuroleptics, neuromuscle blockers, antispasmodics, antihistamines, antiallergics, cardiotonics, antiarrhythmics, diuretics, hypotensives, vasopressors, antitussives, expectorants, analgesics, thyroid hormones, sexual hormones, glucocorticoid hormones, antidiabetics, antitumour drugs, antibiotics, chemotherapeutics, narcotics, anti-Parkinson drugs, anti-Alzheimer drugs and/or triptans.

5. The kit according to claim 1, wherein the microneedle system is a microneedle system based on glass, SiO2, steel, ceramic, starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohols, poly(lactide-co-glycolide), hyaluronic acid, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan and natural gums.

6. The kit according to claim 1, wherein the microneedle system has microneedles with a length from 100 μm to 600 μm, and/or wherein the microneedle system has 50 to 400 microneedles per cm2.

7. The kit according to claim 1 for use in the treatment of a patient.

8. The kit of claim 1, wherein the water-soluble and/or water-swellable polymer is selected from the group consisting of starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohols, poly(lactide-co-glycolide), hyaluronic acid, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan and natural gums.

9. The kit of claim 1, wherein the microneedle system has microneedles with a length from 250 μm to 350 μm and/or has 200 to 250 microneedles per cm2.

10. The kit of claim 1, wherein the pharmaceutically active ingredient is selected riociguat, THC, cannabidiol, dronabinol, thyroid hormones, and/or insulin.

11. The kit of claim 1, wherein the pharmaceutically active ingredient has a water solubility of less than 1.0 mg/ml at 20° C.

12. The kit of claim 1, wherein the oral thin film has an area density of 40-300 g/m2.

13. The kit of claim 1, wherein the oral thin film additionally contains at least one auxillary selected from dyes, flavourings, sweeteners, taste-masking agents, surfactants, enhancers, pH regulators, preservatives, antioxidants, and/or plasticisers.

* * * * *